(12) United States Patent
Alfano et al.

(10) Patent No.: US 6,631,289 B2
(45) Date of Patent: Oct. 7, 2003

(54) SYSTEM AND METHOD OF FLUORESCENCE SPECTROSCOPIC IMAGING FOR CHARACTERIZATION AND MONITORING OF TISSUE DAMAGE

(75) Inventors: Robert R. Alfano, Bronx, NY (US); Jing Tang, Allston, MA (US); Ping Pei Ho, Great Neck, NY (US)

(73) Assignee: Research Foundation of CUNY, New York, NY (US)

( * ) Notice: Subject to any disclaimer, the term of this patent is extended or adjusted under 35 U.S.C. 154(b) by 238 days.

(21) Appl. No.: 09/767,125

(22) Filed: Jan. 22, 2001

(65) Prior Publication Data

US 2002/0002337 A1 Jan. 3, 2002

Related U.S. Application Data

(60) Provisional application No. 60/177,229, filed on Jan. 20, 2000.

(51) Int. Cl.[7] .................................................. A61B 6/00
(52) U.S. Cl. ........................ 600/476; 600/473; 600/310; 356/432; 250/341.1; 436/63; 436/172
(58) Field of Search ................................ 600/476, 473, 600/477, 478, 479, 480, 310; 356/432, 436, 441, 446; 435/34; 250/341.1, 358.1; 436/63, 64, 172, 164; 128/898

(56) References Cited

U.S. PATENT DOCUMENTS

| | | | | |
|---|---|---|---|---|
| 5,042,494 A | * | 8/1991 | Alfano | 600/477 |
| 5,290,272 A | * | 3/1994 | Burnstein et al. | 128/898 |
| 5,348,018 A | * | 9/1994 | Alfano et al. | 600/476 |
| 5,413,108 A | * | 5/1995 | Alfano | 600/478 |
| 5,467,767 A | * | 11/1995 | Alfano et al. | 600/476 |
| 5,474,910 A | * | 12/1995 | Alfano | 435/34 |
| 5,769,081 A | * | 6/1998 | Alfano et al. | 600/476 |
| 5,849,595 A | * | 12/1998 | Alfano et al. | 436/164 |
| 5,983,125 A | * | 11/1999 | Alfano et al. | 600/473 |
| 6,080,584 A | * | 6/2000 | Alfano et al. | 436/63 |
| 6,091,985 A | * | 7/2000 | Alfano et al. | 600/476 |
| 6,208,886 B1 | * | 3/2001 | Alfano et al. | 600/473 |
| 6,221,068 B1 | * | 4/2001 | Fried et al. | 128/898 |

* cited by examiner

*Primary Examiner*—Teresa Walberg
*Assistant Examiner*—Fadi H. Dahbour
(74) *Attorney, Agent, or Firm*—F. Chau & Associates, LLP (57) ABSTRACT

A method for monitoring a biological tissue includes illuminating the tissue, including a fluorophore, with a wavelength of light, the wavelength selected for exciting the fluorophore, determining a fluorescent emission of the fluorophore, the emission indicating the presence of the fluorophore, and correlating an emission of the fluorophore to an extent and degree of damage to the tissue. Damage to the tissue includes a breakdown of the fluorophore, resulting in a reduced level of emission. The fluorophore can include one of collagen and elastin. The fluorophore can include tryptophan, nicotinamide adenine dinucleotide, flavin and porphyrin. Correlating the emission of the fluorophore to the extent and degree of damage further includes processing a correlation of the emission over time, controlling the power of a laser welder based on the processed correlation, and preventing overheating of the tissue by the laser welder.

21 Claims, 9 Drawing Sheets

SYSTEM AND METHOD OF FLUORESCENCE SPECTROSCOPIC IMAGING FOR CHARACTERIZATION AND MONITORING OF TISSUE DAMAGE

This application claims the benefit of Provisional Application No. 60/177,229, filed Jan. 20, 2000.

BACKGROUND OF THE INVENTION

1. Field of the Invention

The present invention relates to the use of fluorescence spectroscopic imaging, more particularly to the use of fluorescence spectroscopic imaging to diagnose tissue damage.

2. Description of Related Art

Proper characterization of tissue damage (e.g., burns and cuts) is needed for determining an appropriate level of treatment. For example, superficial, partial thickness burns typically heal with conservative management impairment. However, for a burn wound that penetrates the full-thickness of the dermis, surgical intervention may be needed to remove damaged tissue and to cover the wound. Therefore, the characterization of tissue damage as, for example, a superficial versus a penetrating burn, is important for determining a treatment.

Prior methods of tissue damage characterization have proved to be unreliable and subject to human error. Clinical appraisals of burn damage, including wound depth, are based on observable tissue color and sensitivity. Studies have shown that even an experienced surgeon may be unable to correctly categorize burn depth in as many as one-third of wounds. Histological sections are an alternative to clinical appraisals and can be used to determining burn wound depth. However, sectioning has been criticized because of its invasive nature, the need for multiple biopsies, sampling error, delay in diagnosis due to fixation time and the need for an experienced pathologist.

Advances in surgical techniques have compounded the problem of tissue damage characterization. For example, laser tissue welding implements a laser beam to join tissues without sutures, thus, a surgeon or other medical personnel needs to characterize the treatment as well as the damage. This distinction can be difficult to make using known techniques.

Tissue welding can also be referred to as tissue fusion or vessel anastomosis. Tissue welding uses laser light energy to activate photo-thermal bonds and/or photo-chemical bonds within targeted tissues. Laser tissue welding can be used alone or in combination with sutures and/or staples to improve strength and/or sealing characteristics. Besides lasers, which operate with wavelengths in the ultra violet, visible and infrared electromagnetic spectrums, other forms of energy, such as radio and microwave frequencies, can be used to join tissues by fusing component proteins.

Laser tissue welding has many advantages over conventional suture techniques, such as a reduction in foreign body reaction (e.g., to sutures, staples, etc.), increased rate of healing, lower constriction of tissues and reduced surgical time. Although success has been achieved in experimental and clinical applications, previous work indicates that the bursting strength of laser assisted blood vessel anastomoses is less than that of a conventional suture. Further, in some cases aneurysm formation can be higher than 6 to 29 percent. One reason for these disadvantages is that the intensity of laser irradiation on a weld site is not well proportioned to the tissue damage, therefore, overheating of the tissue can occur. In order to proportion the laser to the damage, precise tissue damage characterization is needed.

Other laser therapies, such as laser angioplasty, laser recanalization, laser photocoagulation and laser interstitial hyperthemia, also depend on heating a target area. When the photons are absorbed by the tissue, the energy is transformed into heat causing the temperature to rise in the region of adsorption (excited region). One or more photon excitations can lead to protein denaturation, coagulation, and/or ablation.

All heating therapies depend on the selective control of thermal energy delivery and the degree of thermal tissue damage. Therefore, a need exists for a system and method for in situ detection and characterization of tissue damage and treatment.

SUMMARY OF THE INVENTION

A method for monitoring a biological tissue is provided, including the steps of illuminating the tissue, including a fluorophore, with a wavelength of light, the wavelength selected for exciting the fluorophore, determining a fluorescent emission intensity of the fluorophore, the emission indicating the presence of the fluorophore, and correlating an emission of the fluorophore to an extent and a degree of damage to the tissue.

Damage to the tissue includes a breakdown of the fluorophore, resulting in a reduced intensity of emission. The fluorophore can include one of collagen and elastin. The fluorophore can include tryptophan, nicotinamide adenine dinucleotide, flavin and porphyrin.

Correlating the emission of the fluorophore to the extent and degree of damage further includes correlating the emission over time, controlling the power of a laser welder based on the correlation, and preventing overheating of the tissue by the laser welder. The laser tissue welder implements a beam of light having a bandwidth in the absorption bands of water.

The method further includes the step of selecting a wavelength based on the tissue's native concentration of one or more fluorophores, wherein a fluorophore of the highest native concentration is selected for correlation to the extent and degree of damage.

The step of determining a fluorescent emission intensity further comprises the step of determining a relative concentration of the fluorophore over time. The method can further monitor the damage based on the correlation. The damage can include, among others, thermal damage including electrocution, chemical burns, blunt trauma, cuts, and scrapes.

According to an embodiment of the present invention, a method for monitoring a biological tissue is provided. The method illuminates the tissue including collagen with an illumination bandwidth of about 10 nm to about 100 nm of light and a wavelength between about 340 nm to about 380 nm. The method determines a fluorescent emission intensity of the collagen at an emission wavelength of about 380 nm, an intensity of emission indicating the presence and relative amounts of the collagen over time. Further, the method correlates an emission of the collagen to an extent and a degree of thermal damage to the tissue over time. The method controls the power of a laser welder based on the processed correlation and prevents overheating of the tissue by the laser welder. Similarly, emissions of elastin can be monitored, but at longer wavelengths. These methods correlate an emission intensity in real time and/or in situ.

The laser tissue welder can implement a beam of light having a wavelength in the absorption bands of water. The laser tissue welder can implement a beam of light having a wavelength in the absorption bands of collagen.

According to an embodiment of the present invention a monitoring device is provided for detecting thermal damage to a biological tissue and controlling a laser tissue welder. The device includes an illumination device providing a light, a filter provided adjacent to the illumination device to reduce the heat of the light, an optical fiber for directing the filtered light toward the tissue, and a narrow band filter for selecting a bandwidth of light from the filtered light, the bandwidth selected for exciting an emission from a fluorophore of the tissue. The device also includes a camera for collecting a fluorescent emission from the fluorophore, the emission in response to the selected bandwidth of light, a processor for detecting a variation in an emission intensity over time and in response to treatment by the laser tissue welder, and a control means for varying the power of the laser tissue welder in response to a control signal from the processor.

The processor further includes a correlation means for determining the extent and the degree of the thermal damage. The processor can detect a relative concentration of the fluorophore int eh tissue over time.

The laser tissue welder implements a light beam having a wavelength between about 1150 nm and about 1500 nm. The laser can be a Cunyite laser, a Forsterite laser, or similar tissue welding laser having a light beam with a wavelength selected for the absorption bands of water and/or a fluorescent protein.

BRIEF DESCRIPTION OF THE DRAWINGS

Preferred embodiments of the present invention will be described below in more detail, with reference to the accompanying drawings.

DETAILED DESCRIPTION OF PREFERRED EMBODIMENTS

According to an embodiment of the present invention, fluorescence spectroscopy can be used to measure the of electronic transition of fluorophores and chromophores in complex tissue structures. There are several natural fluorophores that exist in tissue which, when excited by ultraviolet light, fluoresce in the ultraviolet and visible regions of the electromagnetic spectrum.

According to an embodiment of the present invention, the fluorescence of proteins in tissue, and in particular, observable variations in the fluorescence as the result of exposure to various wavelengths of light, can be used to characterize tissue damage and repair. A reduction in protein fluorescence, for example, collagen or elastin emissions, can be used to determine the spatial extent of tissue damage as well as the degree of damage (e.g., the degree to which tissue has been welded). Tissue damage can include, among other things, thermal damage (including electrocution), chemical burns (e.g., acid burns), blunt trauma, cuts and scrapes. The present invention contemplates any tissue damage which manifests as a change in the concentration of a protein exhibiting fluorescence, regardless of whether the change is an increase or decrease.

Collagen and elastin are examples of photo-active molecules found in most organic tissue. Collagen is an abundant animal protein found in mammals. Collagen contributes to the structural framework of tissues in most organs. Elastin is a protein that contributes to the structure and development of many tissues. Native fluorescence imaging may be performed with selected emission and excitation wavelengths to detect these and/or other proteins.

Figure 1A:
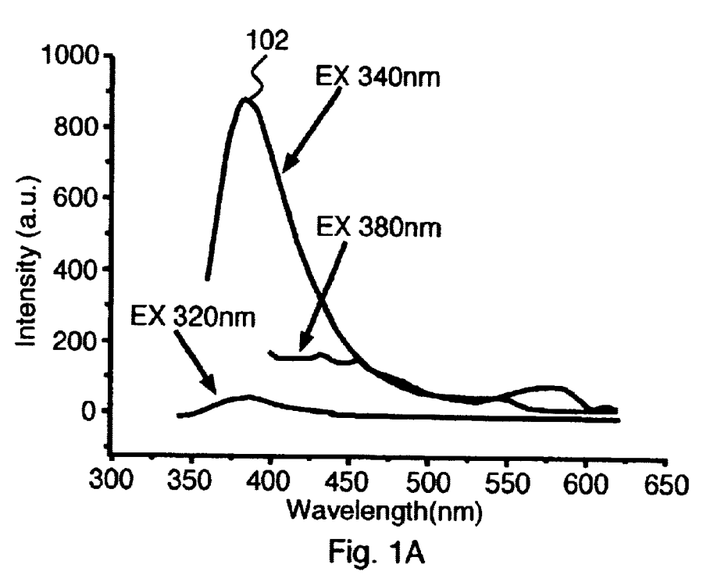
FIG. 1a shows the fluorescence spectra of collagen excited by different wavelengths.
Figure 1B:
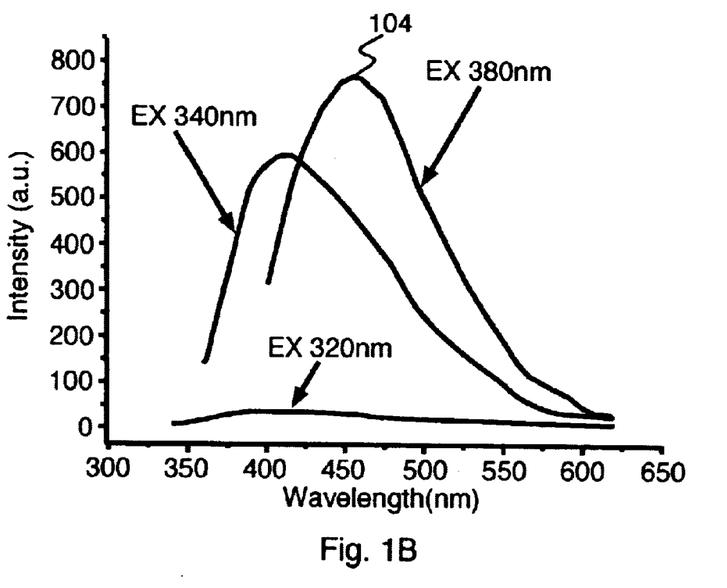
FIG. 1b shows the fluorescence spectra of elastin excited by different wavelengths.

Referring to FIGS. 1a and 1b, the emission spectra of collagen and elastin are shown respectively, excited with 320 nm, 340 nm and 380 nm lights. An emission wavelength ($\lambda_e$) of 380 nm with excitation wavelength ($\lambda_{ex}$) of 340 nm was selected for collagen imaging 102. For elastin imaging, $\lambda_e$=450 nm and $\lambda_{ex}$=380 nm 104. It should be noted that any excitation wavelength producing an emission wavelength dependent on the presence or absence of a photo-thermal or photo-chemical bond may be used.

Figure 2:
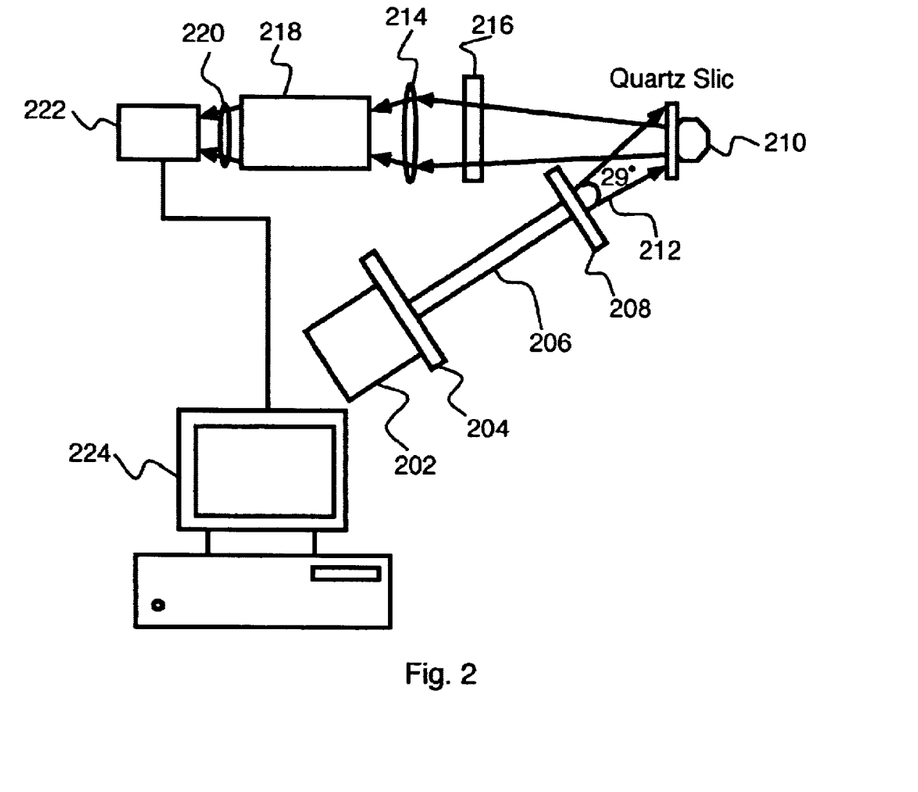
FIG. 2 is an illustrative diagram of a fluorescence imaging system.

Referring to FIG. 2, an illustrative diagram of a fluorescence spectroscopic imaging system in accordance with an embodiment of the present invention. A light beam from a high-intensity xenon lamp 202 (e.g., 300W) is sent through a broad band filter 204 to reduce the heat. The light beam is then transmitted by an optic fiber (excitation fiber) 206 to a narrow band filter (excitation filter) 208 prior to illuminating the sample or tissue 210. The central portion of the bandwidth light beam 212 (e.g., about 10 nm) is used to illuminate the sample 210. The samples resulting fluorescence can be collected by an F=105 mm ultraviolet (UV) camera lens 214 in a back-scattering geometry. A narrow band filter (emission filter) 216 can be inserted at the front of the lens 214 for fluorescence imaging of the sample 210. After the signal was amplified by an image intensifier 218, the fluorescence image can be re-imaged with a second lens 220 onto a charged-coupled device (CCD) camera 222. Those skilled in the art will recognize in view of the present disclosure that other systems and configurations can be used to image a fluorescence image in accordance with the present invention.

Three pictures per second can be obtained from this imaging system. To improve the signal-to-noise ratio, each image can be averaged over several pictures (e.g., ten). A personal computer 224 can be used to digitize and analyze the image, though any processor can be used. A control software generates and displays the resulting fluorescence maps.

Figure 3:
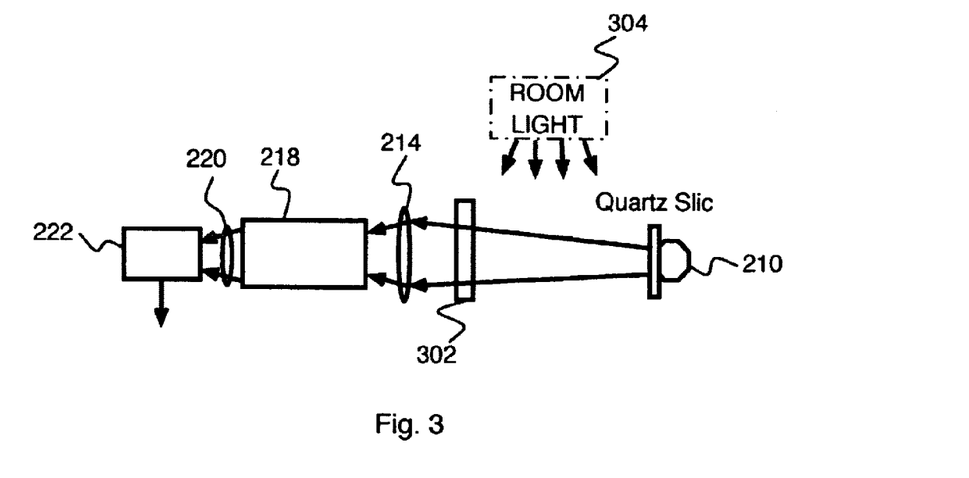
FIG. 3 is an illustrative diagram of a daylight illuminated photography system.

The setup used for daylight illuminated photography of the joint is shown in FIG. 3. A glass plate 302 is placed in front of the second lens 214, replacing the emission filter 216 of FIG. 2, to obtain the same focus and image size as in fluorescence imaging. The sample was illuminated with ambient light, e.g., room lights 304.

Figure 4:
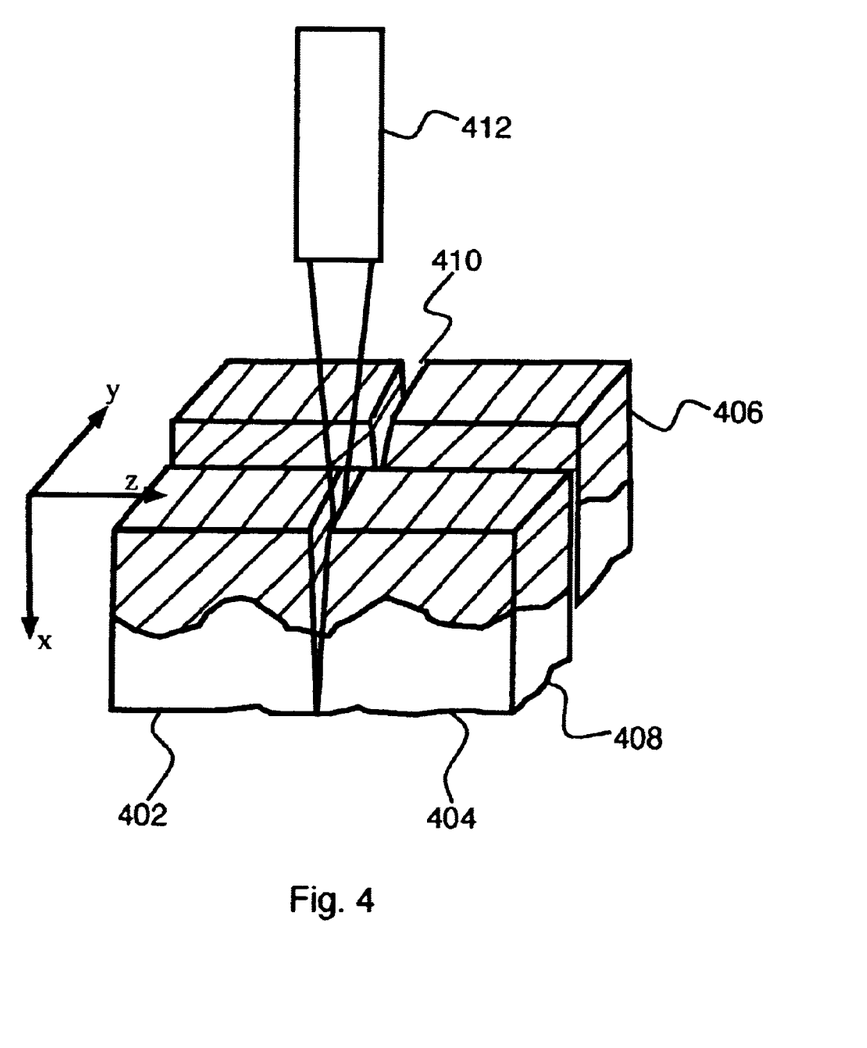
FIG. 4 shows a repaired tissue sample for cross-section fluorescence imaging.

Referring to FIG. 4, two skin pieces (402 and 404), about 2 to 2.5 mm thick were placed, free standing, border-to-border on a translation stage. The dermal layers are shown 406 as well as the subcutaneous tissue 408. Laser tissue welding was performed on the region between the two pieces 410 by scanning the laser irradiation. The stage was moved forward at approximately 5 mm/30 sec., then back at the same speed at the same length. A 5 mm fusion line was formed. No conventional suture was performed. The total exposure time was 5 mm/min. A Cunyite $Cr^{4+}:Ca_2GeO_4$ tunable laser (412) at 1,430 nm, and a Forsterite $Cr^{4+}:M_{g2}SiO_4$ tunable laser (412) at 1,250 nm were used for laser tissue welding (n=10 for each group). The energy fluencies were 10.5 kj/cm$^2$ and 19.1 kj/cm$^2$, respectively. The main mechanism of $Cr^{4+}$ laser (Forsterite and Cunyite) tissue welding uses the absorption bands of water, in the spectral region of about 1,150 nm to about 1,500 nm, to heat and bond tissue, changing the molecular structure of component proteins, e.g., collagen.

After laser tissue welding was performed, the surface of skin sample was mounted in a quartz slide for native collagen fluorescence imaging as well as daylight illuminated photography. The sample was kept in −20° C. for 15 min. While the sample was frozen, a cross-section (X-Z plane, see FIG. 4) through the center of the welded line 410 and perpendicular to Z-Y plane was selected for imaging the welded region. The fluorescence imaging and daylight illuminated photography were performed on the cut cross-section of the joint region of the sample on the X-Z surface (FIG. 4).

In another example, a tendon was implemented as the sample. Tendon tissue is a rich-collagen biological test medium. The sample was cut into a 7×7 mm square, about 5 mm in height. Argon laser irradiation was performed perpendicularly to the surface of the bovine tendon sample for a duration of 3, 6, 9, 12 and 15 sec., respectively (n=6 each time group). The sample were mounted in a quartz slide for spectral analysis and daylight illuminated photography. After native fluorescence imaging and photography were performed on the surface of the sample, the sample was kept at −20° C. for 15 min. A cross-section through maximum diameter of the lesion was made. In addition, native fluorescence imaging and photography were performed on the cross-section of the sample at room temperature.

After spectral analyses and photography, the tissue samples (referring to the skin and tendon samples) were fixed in 10 percent phosphate buffered formalin. The tissues were dehydrated in graded ethanol solution and xylene, and embedded in paraffin. Each of the lesions was sectioned at 5 μm. The sections were treated with Gill's hematoxylin eosin, and picrosirius red F3BA stains. The specimens stained with picrosirius red F3BA were observed with a polarizing microscopic (e.g., a Reichert, Veins, Austria). The other specimens were observed with normal optical microscopic (e.g., Vanox-T, Olympus, Japan). Both microscopes were equipped with a color video camera with three CCD chips (e.g., DXC-97 MD, Sony, Japan) for obtaining histology images.

According to an embodiment of the present invention, fluorescence spectroscopic imaging can be implemented at selected emission and excitation wavelengths to cause spectral protein emissions. Because light and heat cause protein breakdown, the emissions can be used as an indicator of thermal damage in tissues. Further, the extent (e.g., spatial) of the damage can be precisely determined. Proteins exhibiting fluorescence (fluorophores) include, for example, collagen, elastin, tryptophan, nicotinamide adenine dinucleotide (NADH), flavin and porphyrin. After being treated with a laser, these proteins exhibit reduced fluorescence emissions.

The region of collagen or elastin loss can be directly observed in fluorescence spectroscopic imaging at selected emission and excitation wavelengths, due to collagen and/or elastin denaturation caused by heating, for example, laser heating. The change in fluorescence intensity can be confirmed by histology with picrosirius red F3BA stain observed under polarizing microscopic and orcein stain (described above).

Figure 5A:
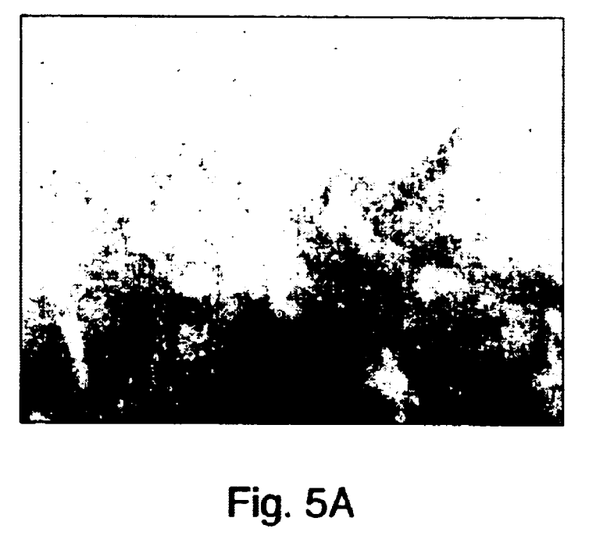
FIG. 5a shows a surface images of welded tissue, wherein two pieces of tissue were completely welded.
Figure 5B:
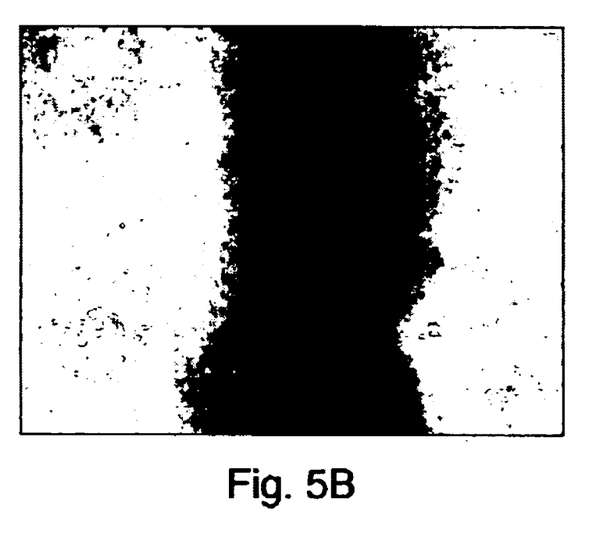
FIG. 5b shows the tissue of FIG. 5a using collagen fluorescence imaging.

A daylight illuminated photograph of the laser tissue welding region on a sample surface is shown in FIG. 3. The two pieces of skin were completely welded. The welded site is invisible in a daylight illuminated photograph, see for example, FIG. 5a. However, the welded region may be seen as a black line in a fluorescence image (FIG. 5b) due to the protein denaturation caused by laser heating and the consequent loss of fluorescence. Thus, a welded site becomes a fluorescence void.

Figure 6A:
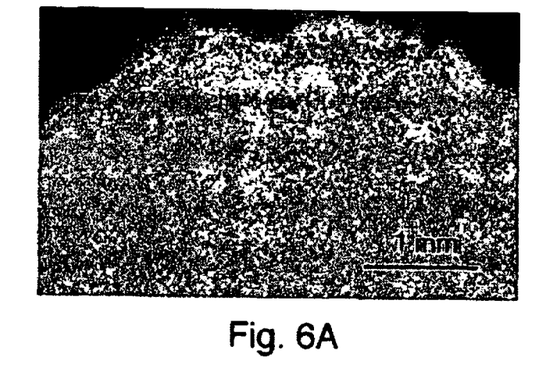
FIG. 6a shows a cross-section of welded tissue using daylight illumination.
Figure 6B:
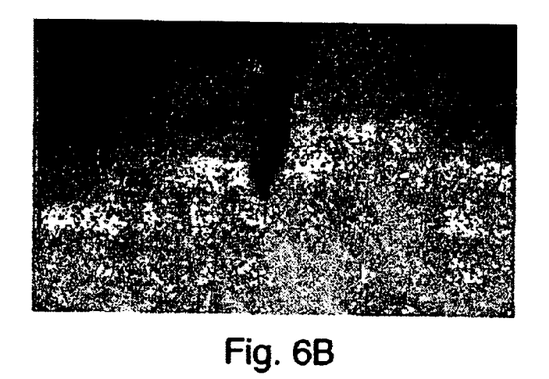
FIG. 6b shows the tissue of FIG. 6a using collagen fluorescence imaging.
Figure 6C:
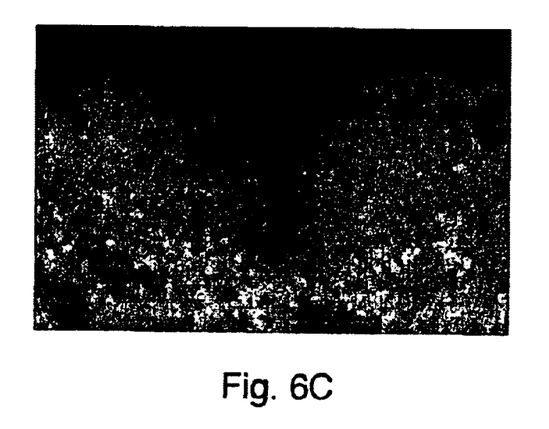
FIG. 6c show the tissue of FIG. 6a using a histological cross-section stained with picrosirius red F3BA and viewed under polarize light.

A depth cross-section of the welded sample is shown by daylight illuminated photography, fluorescence spectroscopic imaging and histological imaging in FIGS. 6a, 6b and 6c, respectively. The welded site was not evident in FIG. 6a, a daylight illuminated photograph. On the fluorescence spectroscopic image (FIG. 6b), the welded site became a fluorescence void, and appears as a crater, due to the collagen or elastin denaturation by laser heating and the consequent loss of fluorescence. The size of the crater in the elastin fluorescence spectroscopic image is less than that in the collagen image. In both the collagen and elastin images, the epidermal layer, the dermal layer, and the subcutaneous layer of the skin sample can be identified by different fluorescence intensities. The crater depth and size in collagen images (FIG. 6b) are substantially similar to the thermal damage depth and size as determined in the histological samples with the picrosirius red F3BA stain observed under polarized light (FIG. 6c).

Figure 7A:
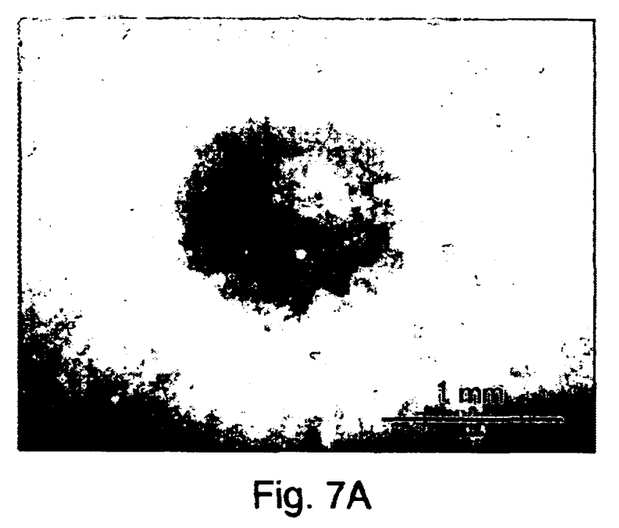
FIG. 7a shows the surface of a tissue sample after irradiated by argon laser using daylight illuminated photography.
Figure 7B:
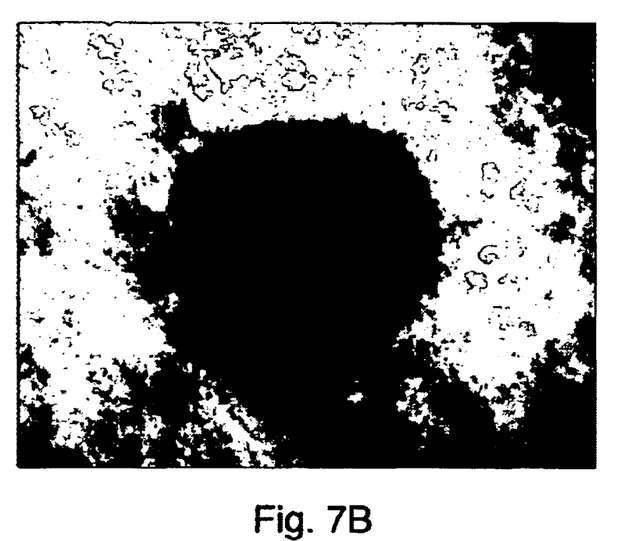
FIG. 7b shows the tissue of FIG. 7a using native fluorescence imaging.
Figure 8A:
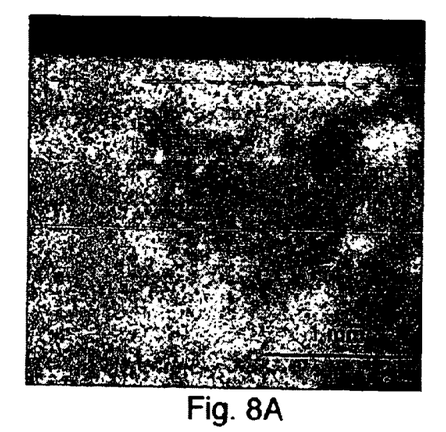
FIG. 8a shows a cross-section of a tissue sample after irradiated by argon laser using daylight illuminated photography.
Figure 8B:
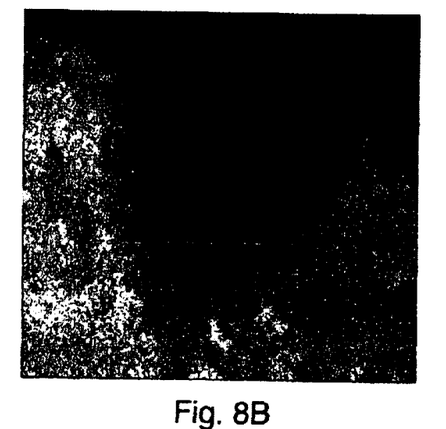
FIG. 8b shows the tissue of FIG. 8a using native fluorescence imaging.
Figure 8C:
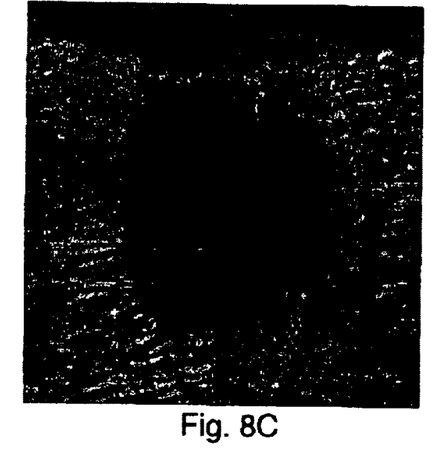
FIG. 8c show the tissue of FIG. 8a using a histological cross-section stained with picrosirius red F3BA and viewed under polarize light.

Daylight illuminated photography and native fluorescence imaging of the surface of the damaged tendon sample are shown in FIGS. 7a and 7b. The corresponding cross-sectional images from the tissue and histological images are shown in FIGS. 8a, 8b, and 8c. Due to the denaturation of collagen, there is a loss of fluorescence. The fluorescence images in FIGS. 7b and 8b show the thermal region. The region of thermal damage becomes dark in the fluorescence image. A narrow zone of gradual fluorescence loss can be seen between the normal and damaged areas. The region of thermal damage in the native fluorescence images (FIGS. 7b, 8b) is much clearer than that of daylight illuminated photography (FIGS. 7a, 8a).

The diameters of the thermal damage region on the surface, measured from the native fluorescence image and daylight illuminated photograph are listed in Table 1. The diameter (mm) of the thermally damaged regions irradiated is shown at different exposure times at a power density of 274 W/cm$^2$.

TABLE 1

| Method/<br>Time<br>(Sec) | 3 | 6 | 9 | 12 | 15 |
|---|---|---|---|---|---|
| Fluor-<br>escence<br>imaging | 1.40 ± .04 | 1.84 ± .03 | 1.95 ± .04 | 2.39 ± .17 | 2.81 ± .04 |
| Photo-<br>graph | 1.09 ± .02* | 1.79 ± .03 | 1.89 ± .05 | 2.51 ± .12 | 2.94 ± .02 |

*p < 0.01

These is a statistic difference between fluorescence image and daylight illuminated photograph ($F=10.30497$, $p=0.00933$) measured from 3-sec-irradiation group.

FIG. 8c shows a histological cross-section of the sample stained using picrosirius red F3BA was polarized light. The normal collagen fibers not in laser treated area appear yellow/orange. Some tissue structures disappeared in laser treated region and became homogenized after laser irradiation. The collagen in the damaged region shows evidence of denaturation and loss of its natural birefringence. This region became clear (de-colored) and darker. The damaged region in the slide is similar to that shown in the native fluorescence image (FIG. 8b). Both images show stronger thermal damage on the treated tissue region in the center of the damaged region and less below the surface. After a tissue-shrinkage correction factor of 1.15 is multiplied, the maximum depth of the damaged region was measured on the slides stained using picrosirius red F3BA illuminated with polarized light. Table. 2 lists the depth (mm) of thermal tissue damage irradiated at different exposure times at a power density of 274 W/cm$^2$ measured by native fluorescence imaging, histology and photography.

TABLE 2

| Method/<br>Time<br>(Sec) | 3 | 6 | 9 | 12 | 15 |
|---|---|---|---|---|---|
| Fluor-<br>escence<br>imaging | 1.07 ± .23 | 1.57 ± .12 | 1.68 ± .23 | 1.82 ± .39 | 2.13 ± .28 |
| Histo-<br>logy | 1.05 ± .15 | 1.52 ± .22 | 1.70 ± .34 | 1.80 ± .27 | 2.15 ± .31 |
| Photo-<br>graph | 0.82 ± .23* | 1.61 ± .15 | 1.63 ± .17 | 1.77 ± .34 | 2.08 ± .29 |

*p < 0.05

There is a difference between fluorescence image and daylight illuminated photograph ($F=3.5974$, $p=0.03158$) in 3 sec. irradiation group.

According to an embodiment of the present invention, the optical imaging system shown in FIG. 2 uses an illumination beam from a high-intensity xenon lamp source passed through a narrow band filter (excitation filter) to ensure UV monochromatic irradiation. Fluorescence from the sample can be collected using a UV lense. The collected fluorescence can form an image on a CCD camera after passing through an emission filter.

Real-time fluorescence imaging can be used to monitor the condition of welded site in situ. No fluorescence intensity change on the welded site means that the tissue has not been heated by laser beam and/or the welding was not effective.

Figure 9:
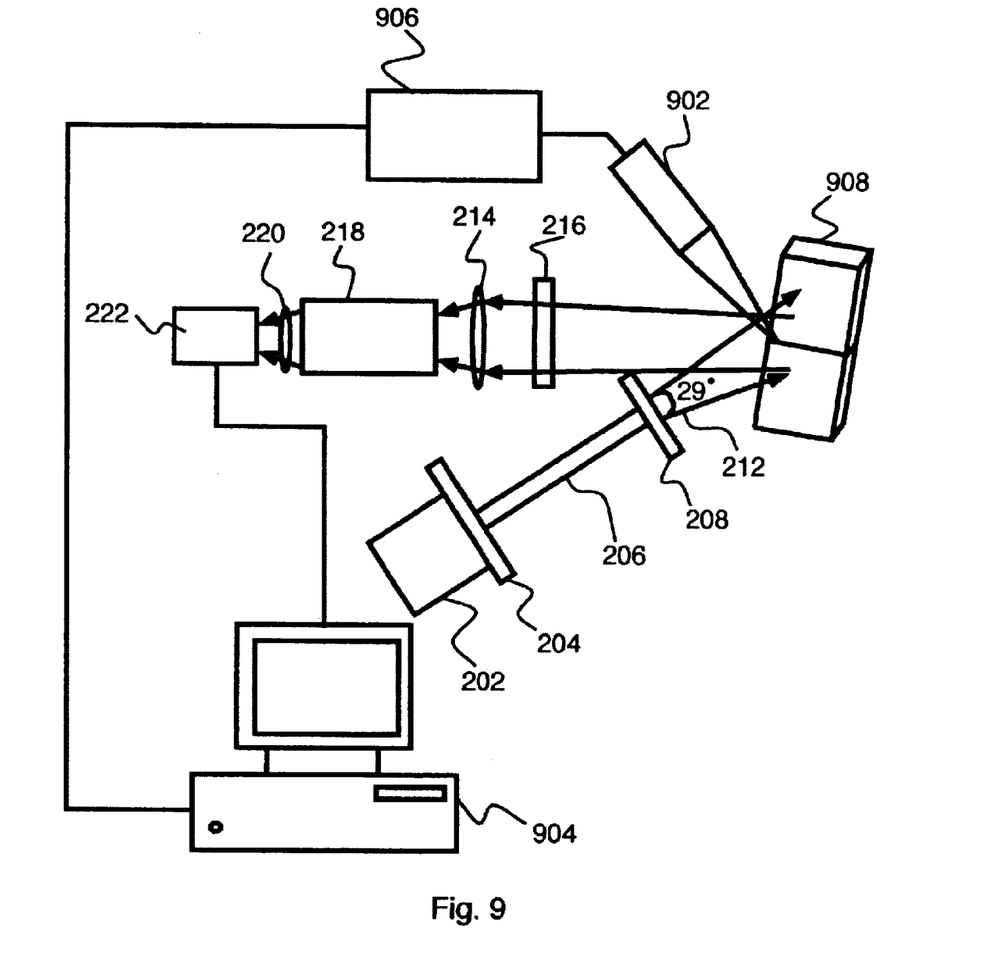
FIG. 9 is an illustrative diagram of an imaging system for preventing overheating of tissue during laser tissue welding.

A perceived change in fluorescence intensity can also be used as a feed-back signal in an automatic laser tissue welding system. (See FIG. 9.) The power of welding laser 902 can be automatically controlled via a processor 904 and controller 906 when a change in fluorescence intensity from the welded tissue 908 is perceived. Thus, collateral tissue damage can be avoided, specifically, overheating of the welded tissue 908.

From the teaching of the relationship between tissue fluorescence intensity (variation) and thermal damage of shown in FIGS. 5b, 6b, 7b, and 8b, the present invention can be used to monitor thermal damage and to measure the depth of laser tissue penetration from a laser or other heating sources. Before the laser ablation surgery or other heating sources treat on the tissue, tissue fluorescence is visible on fluorescence imaging. After the time of the tissue to be heated at the temperature over 65° C., the intensity of the fluorescence from the tissue will be reduced. This change can be determined for treated tissue in situ. The tissue thermal damage or the depth of laser penetration can be displayed and calculated by image processing by the processor 904. The present invention can also be used to detect the size of a burned tissue area and to estimate the depth of burned wound. If the fluorescence intensity of burned tissue is reduced the tissue has damaged thermally.

Having described embodiments for non-invasive monitoring of biological tissue via fluorescence, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

What is claimed is:

1. A method for monitoring a biological tissue comprising the steps of:
   illuminating the tissue including a fluorophore with a wavelength of light, the wavelength selected for exciting the fluorophore;
   determining a fluorescent emission intensity of the fluorophore, the emission indicating the presence of the fluorophore;
   determining a relative concentration of the fluorophore over time according to the emission; and
   correlating an emission of the fluorophore to an extent and a degree of damage to the tissue.

2. The method of claim 1, wherein damage to the tissue includes a breakdown of the fluorophore, resulting in a reduced intensity of emission.

3. The method of claim 1, wherein the fluorophore includes one of collagen and elastin.

4. The method of claim 1, wherein the fluorophore includes one of tryptophan, nicotinamide adenine dinucleotide, flavin and porphyrin.

5. The method of claim 1, wherein the step of correlating the emission of the fluorophore to the extent and degree of damage further comprises the steps of:
   correlating the emission over time to produce a correlation of emission to the extent and degree of damage to the tissue;

controlling the power of a laser tissue welder based on the correlation; and preventing overheating of the tissue by the laser tissue welder.

6. The method of claim 5, wherein the laser tissue welder implements a beam of light having a bandwidth in the absorption bands of water.

7. The method of claim 1, further comprising the step of selecting a wavelength based on native concentrations of fluorophores in the tissue, wherein a fluorophore of the highest native concentration is selected for correlation to the extent and degree of damage.

8. The method of claim 1, further comprising the step of monitoring the damage based on the correlation.

9. The method of claim 1, wherein the damage is one of thermal damage, chemical burns, blunt trauma, cuts, wounds and scrapes.

10. A method for monitoring a biological tissue comprising the steps of:

illuminating the tissue including collagen with an illumination bandwidth of about 10 nm to about 100 nm of light and a wavelength between about 340 nm to about 380 nm;

determining a fluorescent emission of the collagen at an emission wavelength of about 380 nm, an intensity of emission indicating the presence and the relative concentration of the collagen over time;

correlating an emission of the collagen to an extent and a degree of thermal damage to the tissue over time;

controlling the power of a laser tissue welder based on a correlation; and preventing overheating of the tissue by the laser tissue welder.

11. The method of claim 10, wherein the correlation is made in real time.

12. The method of claim 10, wherein the correlation is made in situ.

13. The method of claim 10, wherein the laser tissue welder implements a beam of light having a wavelength in the absorption bands of water.

14. The method of claim 10, wherein the laser tissue welder implements a beam of light having a wavelength in the absorption bands of collagen.

15. A monitoring device for detecting thermal damage to a biological tissue and controlling a laser tissue welder comprising:

an illumination device providing a light;

a filter provided adjacent to the illumination device to reduce the heat of the light;

an optical fiber for directing the filtered light toward the tissue;

a narrow band filter for selecting a bandwidth of light from the filtered light, the bandwidth selected for exciting an emission from a fluorophore of the tissue;

a camera for collecting a fluorescent emission from the fluorophore, the emission in response to the selected bandwidth of light;

a processor for detecting a variation in an emission intensity over time and in response to treatment by the laser tissue welder; and a control means for varying the power of the laser tissue welder in response to a control signal from the processor.

16. The monitoring device of claim 15, wherein the processor comprises a correlation means for determining the extent and the degree of thermal damage.

17. The monitoring device of claim 15, wherein the processor for detecting a relative concentration of the fluorophore in the tissue over time.

18. The monitoring device of claim 15, wherein the laser tissue welder implements a light beam having a wavelength between about 1150 nm and about 1500 nm.

19. The monitoring device of claim 15, wherein the laser is one of a Cunyite and a Forsterite laser.

20. A method for laser tissue welding comprising the steps of:

providing a near-infrared laser having a wavelength in the absorption band of water between about 1150 nm and 1500 nm;

applying the near-infrared laser to a tissue to produce a weld;

determining a fluorescent emission intensity of a fluorophore in the tissue, the emission indicating the presence of the fluorophore;

determining a relative concentration of the fluorophore over time according to the emission; and correlating an emission of the fluorophore to an extent and a degree of damage to the tissue.

21. The method of claim 20, wherein the step of correlating the emission of the fluorophore to the extent and degree of damage further comprises the steps of:

correlating the emission over time to produce a correlation of emission to the extent and degree of damage to the tissue;

controlling the power of a laser tissue welder based on the correlation; and preventing overheating of the tissue by the laser tissue welder.

* * * * *